(12) United States Patent
Mauler-Machnik et al.

(10) Patent No.: US 6,559,136 B1
(45) Date of Patent: May 6, 2003

(54) FUNGICIDAL ACTIVE SUBSTANCE COMBINATIONS

(75) Inventors: Astrid Mauler-Machnik, Leichlingen (DE); Ulrike Wachendorff-Neumann, Neuwied (DE); Herbert Gayer, Monheim (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/856,023

(22) PCT Filed: Nov. 8, 1999

(86) PCT No.: PCT/EP99/08558

§ 371 (c)(1),
(2), (4) Date: May 16, 2001

(87) PCT Pub. No.: WO00/30440

PCT Pub. Date: Jun. 2, 2000

(30) Foreign Application Priority Data

Nov. 20, 1998 (DE) .......................... 198 53 559
Aug. 23, 1999 (DE) .......................... 199 39 841

(51) Int. Cl.[7] ................ A01N 43/653; A01N 55/10; A01N 43/54
(52) U.S. Cl. ............... 514/63; 514/259; 514/260; 514/269; 514/270; 514/383; 514/384
(58) Field of Search ................... 514/270, 383, 514/260, 63, 259, 269, 384

(56) References Cited

U.S. PATENT DOCUMENTS 4,438,122 A    3/1984   Holmwood et al. ........ 514/277
4,518,600 A    5/1985   Holmwood et al. ........ 514/256

FOREIGN PATENT DOCUMENTS

| DE | 19 646 407 | 5/1998 |
| EP | 0 627 169 | 12/1994 |
| GB | 2253624 | * 9/1992 |
| WO | 98/25465 | 6/1998 |

OTHER PUBLICATIONS

K.H. Büchel "Pflanzenschutz und Schädlingsbekämpfung" pp. 87, 136, 140, 141, and 146–153, (month unavailable) 1977.

* cited by examiner

Primary Examiner—John Pak
(74) Attorney, Agent, or Firm—Joseph C. Gil; John E. Mrozinski, Jr.; Richard E. L. Henderson

(57) ABSTRACT

Novel active compound combinations of compounds of the formula (I)

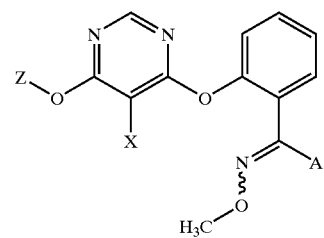

in which

Z, X and A are each as defined in the description with known active compounds and their use for controlling phytopathogenic fungi are described.

5 Claims, No Drawings

FUNGICIDAL ACTIVE SUBSTANCE COMBINATIONS

This application is a 371 of PCT/EP99/08558, filed on Nov. 8, 1999.

The present application relates to novel active compound combinations comprising, on the one hand, pyrimidine derivatives and, on the other hand, other known fungicidally active compounds and being highly suitable for controlling phytopathogenic fungi.

It is already known that pyrimidine derivatives have fungicidal properties (cf. DE-A-19 646 407). The activity of this substance is good; however, at low application rates it sometimes leaves something to be desired.

Furthermore, it is already known that numerous azole derivatives, aromatic carboxylic acid derivatives. morpholine compounds and other heterocycles can be used for controlling fungi (cf. K. H. Büichel "Pflanzenschutz und Sch ädlings-bekämpfung" pages 87, 136, 140, 141 and 146 to 153, Georg Thieme Verlag, Stuttgart 1977). However, the activity of the substances in question is not always satisfactory at low application rates.

It has now been found that the novel active compound combinations of compounds of the general formula (I)

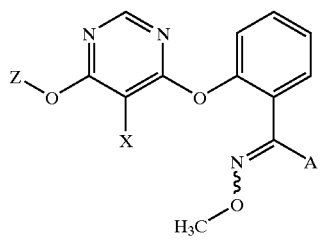

in which
- Z represents optionally substituted phenyl,
- X represents halogen and
- A represents heterocyclyl —COOCH$_3$ or —CO—NH—CH$_3$ and in each case one compound selected from the list of the compounds below 1) spiroxamin
2) quinoxyfen (DE 795)
3) tebuconazole
4) fenpropidin
5) fenpropimorph
6) (R,S)- and (R,R)- and (S,R)- and (S,S)-N-(1-cyano-1,2-dimethylpropyl)-2-(2,4-dichlorophenoxy)propionamide
7) chlorothalonil (DAC 2787)
8) triadimefon
9) triadimenol
10) epoxiconazole
11) metconazole
12) fluquinconazole
13) cyproconazole
14) penconazole
15) kresoximmethyl
16) azoxystrobin
17) cyprodinil
18) iminoctadiene triacetate (Befran)
19) flusilazole (Harvesan)
20) prochloraz (Sportak)
21) propiconazole (Desmel)
22) bitertanol (KWG 0599)
23) imidacloprid (NTN 33893)
24) dichlofluanid (Euparen)
25) tolylfluanid (Euparen M)
26) metalaxyl (Ridomil)
27) fenpiclonil
28) difenoconazole
29) fludioxonil
30) carbendazim, benomyl
31) fuberidazol
32) imazalil
33) triazoxide (SAS 9244)
34) cyfluthrin (Pyrethroid)
35) guazatine
36) acibenzolar-S-methyl (Bion)
37) pencycuron (Monceren)
38) flutolanil (Moncut)
39) tricyclazole (Beam)
40) propineb (Antracol)
41) procymidone (Sumisclex)
42) mancozeb
43) folpet (Phaltan)
44) dimetomorph
45) cymoxanil (Curzate)
46) fosetyl-Al (Aliette)
47) famoxadone
48) pyrimethanil
49) mepanipyrim
50) iprovalicarb
51) fenhexamid
52) carpropamid
53) fluazinam
54) captan
55) chinomethionat (Morestan)
56) fenamidone (RP 7213)
57) clothianidin
58) thiacloprid
59) diacloden
60) acetamiprid
61) MTI 334
62) sulphur
63) copper
64) rovral
65) ronilan
66) rabcide
67) hinosan
68) coratop
69) 2-(1-chloro-cyclopropyl)-1-(2-chlorophenyl)-3-(5-mercapto-1,2,4-triazol-1-yl)-propan-2-ol
70) 1-(3,5-dimethylisoxazol-4-sulfonyl)-2-chloro-6,6-difluoro-[1,3]-dioxolo-[4,5f]-benzimidazole
71) 3-{1-[4-(<2-chlorophenoxy>5-fluoropyrimid-6-yloxy)-phenyl]-1-(methoximino)-methyl}-5,6-dihydro-1,4,2-dioxazine
72) zoxamide
73) cyamidazosulfamide
74) silthiopham
75) trifloxystrobin
76) N-methyl-2-(methoxyimino)-2-[2-([1-(3-trifluoromethyl-phenyl)ethoxy]iminomethyl)-phenyl]acetamide
77) 2-[2-([2-phenyl-2-methoxy-imino-1-methylethyl]imino-oxymethyl)phenyl]-2-methoxy-imino-N-methylacetamide
78) 2-[2-([2-(4-fluorophenyl)-2-methoxyimino-1-methylethyl]-iminooxymethyl)phenyl]-2-methoxyimino-N-methyl-acetamide
79) 2-[4-methoxy-3-(1-methyl-ethoxy)-1,4-diazabuta-1,3-dienyloxymethyl)phenyl-2-methoximino-N-methylacetamide
80) methyl N-(2-[1-(4-chloro-phenyl)pyrazol-3-yloxymethyl]-phenyl)-N-methoxycarbamate
81) 2,4-dihydro-5-methoxy-2-methyl-4-[2-([[1-(3-trifluoro-methylphenyl)ethylidene]-amino)oxy]methyl)phenyl]-3H-1,2,4-triazol-3-one
82) picoxystrobin in a mixing ratio of a compound of the formula (I) to in each case one compound of the formulae 1) to 82) of from 20:1 to 1:50 parts by weight have very good fungicidal properties.

Surprisingly, the fungicidally activity of the active compound combination according to the invention is considerably higher than the sum of the activities of the individual active compounds. An unforeseeable true synergistic effect is present, and not just an addition of activities.

Compounds of the formula (I), in which
Z represents a group

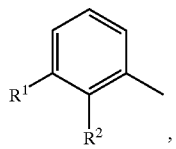

in which
R¹ and R² represent, independently of one another, hydrogen, methyl, ethyl, methoxy, ethoxy, chlorine, bromine, fluorine or cyano,
X represents fluorine and
A represents —CO—NH—CH$_3$,
may be preferably mentioned.

In particular, the compounds of the formula (I), in which
R¹ represents hydrogen and
R² represents methyl, ethyl, methoxy, chlorine, bromine, fluorine or cyano,
and compounds of the formula (I), in which
R¹ represents methyl and
R² represents hydrogen, methyl, ethyl, methoxy, chlorine, bromine, fluorine or cyano,
and compounds of the formula (1), in which
R² represents methyl and
R¹ represents hydrogen, methyl, ethyl, methoxy, chlorine, bromine, fluorine or cyano,
may be mentioned specifically.

The active compounds of the formula (I) are known (cf., for example, DE-A 19 646 407, WO 97-27189 or GB 225 3624).

The active compounds which are furthermore present in the combinations according to the invention are also known. The active compounds are described, for example, in The Pesticide Manual, 11th Edition, British Crop Protection Council (BCPC).

The active compound combinations according to the invention comprise, in addition to at least one active compound of the formula (I), at least one active compound from among the compounds of groups 1) to 82). Additionally, they may also comprise other fungicidally active additives.

If the active compounds in the active compound combinations according to the invention are present in certain weight ratios, the synergistic effect is particularly pronounced. However, the weight ratios of the active compounds in the active compound combinations can be varied within a relatively wide range. In general, the combinations according to the invention comprise the active compound of the formula (I) and the mixing partner in the preferred and particularly preferred mixing ratios given in the table below:

| Mixing partner | Preferred mixing ratio* | Particularly preferred mixing ratio* |
| --- | --- | --- |
| spiroxamin | 10:1 to 1:20 | 5:1 to 1:10 |
| quinoxyfen (DE 795) | 10:1 to 1:20 | 5:1 to 1:10 |
| tebuconazole | 10:1 to 1:10 | 5:1 to 1:5 |
| fenpropidin | 10:1 to 1:20 | 5:1 to 1:10 |
| fenpropimorph | 10:1 to 1:20 | 5:1 to 1:10 |

| Mixing partner | Preferred mixing ratio* | Particularly preferred mixing ratio* |
| --- | --- | --- |
| (R,S)- and (R,R)- and (S,R)- and (S,S)-N(1-cyano-1,2-dimethylpropyl)-2-(2,4-dichlorophenoxy)propionamide | 10:1 to 1:10 | 5:1 to 1:5 |
| chlorothalonil (DAC 2787) | 1:1 to 1:50 | 1:5 to 1:20 |
| triadimefon | 10:1 to 1:10 | 5:1 to 1:5 |
| triadimenol | 10:1 to 1:10 | 5:1 to 1:5 |
| epoxiconazole | 10:1 to 1:10 | 5:1 to 1:5 |
| metconazole | 10:1 to 1:10 | 5:1 to 1:5 |
| fluquinconazole | 10:1 to 1:10 | 5:1 to 1:5 |
| cyproconazole | 10:1 to 1:10 | 5:1 to 1:5 |
| penconazole | 10:1 to 1:10 | 5:1 to 1:5 |
| kresoximmethyl | 10:1 to 1:10 | 5:1 to 1:5 |
| azoxystrobin | 10:1 to 1:10 | 5:1 to 1:5 |
| cyprodinil | 5:1 to 1:20 | 1:1 to 1:10 |
| iminoctadiene triacetate (Befran) | 10:1 to 1:10 | 5:1 to 1:5 |
| flusilazole (Harvesan) | 10:1 to 1:10 | 5:1 to 1:5 |
| prochloraz (Sportak) | 10:1 to 1:10 | 5:1 to 1:5 |
| propiconazole (Desmel) | 10:1 to 1:10 | 5:1 to 1:5 |
| bitertanol | 10:1 to 1:10 | 5:1 to 1:5 |
| imidacloprid | 20:1 to 1:20 | 10:1 to 1:10 |
| dichlofluanid (Euparen) | 1:1 to 1:50 | 1:1 to 1:20 |
| tolylfluanid (Euparen M) | 1:1 to 1:50 | 1:1 to 1:20 |
| metalaxyl (Ridomil) | 10:1 to 1:10 | 5:1 to 1:5 |
| fenpiclonil | 10:1 to 1:10 | 5:1 to 1:5 |
| difenoconazole | 10:1 to 1:10 | 5:1 to 1:5 |
| fludioxonil | 10:1 to 1:10 | 5:1 to 1:5 |
| carbendazim, benomyl | 10:1 to 1:10 | 5:1 to 1:5 |
| fuberidazol | 20:1 to 1:10 | 10:1 to 1:5 |
| imazalil | 20:1 to 1:10 | 10:1 to 1:5 |
| triazoxide (SAS 9244) | 20:1 to 1:10 | 10:1 to 1:5 |
| cyfluthrin (Pyrethroid) | 20:1 to 1:20 | 10:1 to 1:10 |
| guazatine | 10:1 to 1:10 | 5:1 to 1:5 |
| acibenzolar-S-methyl (Bion) | 50:1 to 1:50 | 20:1 to 1:10 |
| pencycuron (Monceren) | 10:1 to 1:10 | 5:1 to 1:5 |
| flutolanil (Moncut) | 10:1 to 1:10 | 5:1 to 1:5 |
| tricyclazole (Beam) | 10:1 to 1:10 | 5:1 to 1:5 |
| propineb (Antracol) | 1:1 to 1:50 | 1:5 to 1:20 |
| procymidone (Sumisclex) | 10:1 to 1:10 | 5:1 to 1:5 |
| mancozeb | 1:1 to 1:50 | 1:5 to 1:20 |
| folpet (Phaltan) | 1:1 to 1:50 | 1:5 to 1:20 |
| dimetomorph | 10:1 to 1:10 | 5:1 to 1:5 |
| cymoxanil (Curzate) | 10:1 to 1:10 | 5:1 to 1:5 |
| fosetyl-al (Aliette) | 10:1 to 1:50 | 1:1 to 1:10 |
| famoxadone | 10:1 to 1:10 | 5:1 to 1:5 |
| pyrimethanil | 5:1 to 1:20 | 1:1 to 1:10 |
| mepanipyrim | 5:1 to 1:20 | 1:1 to 1:10 |
| iprovalicarb | 10:1 to 1:10 | 5:1 to 1:5 |
| fenhexamid | 10:1 to 1:10 | 5:1 to 1:5 |
| carpropamid | 10:1 to 1:10 | 5:1 to 1:5 |
| fluazinam | 10:1 to 1:10 | 5:1 to 1:5 |
| captan | 5:1 to 1:50 | 1:1 to 1:20 |
| chinomethionat (Morestan) | 5:1 to 1:50 | 1:1 to 1:20 |
| fenamidone (RP 7213) | 10:1 to 1:10 | 5:1 to 1:5 |
| clothianidin | 20:1 to 1:20 | 10:1 to 1:10 |
| thiacloprid | 20:1 to 1:20 | 10:1 to 1:10 |
| diacloden | 20:1 to 1:20 | 10:1 to 1:10 |
| acetamiprid | 20:1 to 1:20 | 10:1 to 1:10 |
| MTI 334 | 20:1 to 1:20 | 10:1 to 1:10 |
| sulphur | 20:1 to 1:20 | 10:1 to 1:10 |
| copper | 20:1 to 1:20 | 10:1 to 1:10 |
| rovral | 10:1 to 1:10 | 5:1 to 1:5 |
| ronilan | 10:1 to 1:10 | 5:1 to 1:5 |
| rabcide | 10:1 to 1:10 | 5:1 to 1:5 |
| hinosan | 10:1 to 1:10 | 5:1 to 1:5 |
| coratop | 10:1 to 1:10 | 5:1 to 1:5 |
| 2-(1-chloro-cyclopropyl)-1-(2-chlorophenyl)-3-(5-mercapto-1,2,4-triazol-1-yl)-propan-2-ol | 20:1 to 1:5 | 20:1 to 1:5 |
| 1-(3,5-dimethylisoxazol-4-sulfonyl)-2-chloro-6,6-difluoro-[1,3]-dioxolo-[4,5f]benzimidazole | 50:1 to 1:10 | 20:1 to 1:5 |

-continued

| Mixing partner | Preferred mixing ratio* | Particularly preferred mixing ratio* |
|---|---|---|
| 3-{1-[4-(<2-chloro-phenoxy>5-fluoropyrimid-6-yloxy)-phenyl]-1-(methoximino)-methyl}-5,6-dihydro-1,4,2-dioxazine | 10:1 to 1:10 | 5:1 to 1:5 |
| zoxamide | 50:1 to 1:10 | 20:1 to 1:5 |
| cyamidazosulfamide | 20:1 to 1:5 | 20:1 to 1:5 |
| silthiopham | 20:1 to 1:10 | 20:1 to 1:5 |
| trifloxystrobin | 10:1 to 1:10 | 5:1 to 1:5 |
| N-methyl-2-(methoxyimino)-2-[2-([1-(3-trifluoromethyl-phenyl)ethoxy]iminomethyl)-phenyl]acetamide | 10:1 to 1:10 | 5:1 to 1:5 |
| 2-[2-([2-phenyl-2-methoxy-imino-1-methylethyl]imino-oxymethyl)phenyl]-2-methoxyimino-N-methylacetamide | 10:1 to 1:10 | 5:1 to 1:5 |
| 2-[2-([2-(4-fluorophenyl)-2-methoxyimino-1-methyl-ethyl]-iminooxymethyl)-phenyl]-2-methoxyimino-N-methylacetamide | 10:1 to 1:10 | 5:1 to 1:5 |
| 2-[4-methoxy-3-(1-methyl-ethoxy)-1,4-diazabuta-1,3-dienyloxymethyl)phenyl-2-methoximino-N-methyl-acetamide | 10:1 to 1:10 | 5:1 to 1:5 |
| methyl N-(2-[1-(4-chloro-phenyl)pyrazol-3-yloxy-methyl]phenyl)-N-methoxy-carbamate | 10:1 to 1:10 | 5:1 to 1:5 |
| 2,4-dihydro-5-methoxy-2-methyl-4-[2-([(1-(3-trifluoro-methylphenyl)ethylidene)-amino]oxy]methyl)phenyl]-3H-1,2,4-triazol-3-one | 10:1 to 1:10 | 5:1 to 1:5 |
| picoxystrobin | 10:1 to 1:10 | 5:1 to 1:5 |

*the mixing ratios are based on weight ratios. The ratio is to be understood as active compound of the formula I: mixing partner The active compound combinations according to the invention have very good fungicidal properties and can be employed in particular for controlling phytopathogenic fungi, such as Plasmodiophoromycetes, Oomycetes, Chytridiomycetes, Zygomycetes, Ascomycetes, Basidiomycetes, Deuteromycetes, etc.

The fact that the active compound combinations are well tolerated by plants at the concentrations required for controlling plant diseases permits the treatment of above-ground parts of plants, of propagation stock and seeds, and of the soil.

The active compound combinations according to the invention can be converted into the customary formulations, such as solutions, emulsions, suspensions, powders, foams, pastes, granules, aerosols and microencapsulations in polymeric substances and in coating compositions for seeds, and ULV formulations.

These formulations are produced in a known manner, for example by mixing the active compounds or active compound combinations with extenders, that is liquid solvents, liquefied gases under pressure, and/or solid carriers, optionally with the use of surfactants, that is emulsifiers and/or dispersants, and/or foam formers. If the extender used is water, it is also possible to use, for example, organic solvents as auxiliary solvents. Essentially, suitable liquid solvents include: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water. Liquefied gaseous extenders or carriers are to be understood as meaning liquids which are gaseous at ambient temperature and under atmospheric pressure, for example aerosol propellants such as butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

In the formulations, the active compounds of the formula (I) and the active compound combinations according to the invention can be present as a mixture with other active compounds such as fungicides, insecticides, acaricides and herbicides, and as mixtures with fertilizers or plant growth regulators.

Mixing partners for such mixtures are, for example:
Fungicides:
  2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino-[alpha-(o-tolyloxy)-o-tolyl]-acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, dictomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulphamide, flutolanil, flutriafol, folpet, fosetyl-aluminium, fthalide, fuberidazole, furataxyl, furmecyclox, guazatine, hexachlorobenzene, hexaconazole, hymexazol, imazalil, imibenconazole, iminoctadine, iprobenfos (EBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulphocarb, methfuroxam, metiram, metsulphovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebucanozole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforin, triticonazole, validamycin A, vinclozolin, zineb, ziram.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:

abamectin, abamectin, AC 303 630, acephate, acrinathrin, alanycarb, aldicarb, alphamethrin, amitraz, avermnectin, AZ 60541, azadirachtin, azinphos A, azinphos M, azocyclotin,

*Bacillus thuringiensis*, bendiocarb, benfuracarb, bensultap, betacyfluthrin, bifenthrin, BPMC, brofenprox, bromophos A, bufencarb, buprofezin, butocarboxin, butylpyridaben, cadusafos, carbaryl, carbofuran, carbophenothion, carbosulphan, cartap, CGA 157 419, CGA 184699, chloethocarb, chlorethoxyfos, chlorfenvinphos, chlorfluazuron, chiormephos, chlorpyrifos, chlorpyrifos M, cis-resmethrin, clocythrin, clofentezine, cyanophos, cycloprothrip, cyfluthrin, cyhalothirin, cyhexatin, cypermetlrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulphoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mervinphos, mesulphenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamdon, phoxim, pirimicarb, pirimiphos M, pirimiphos A, profenofos, promecarb, propaphos, propoxur, prothiofos, prothoate, pymetrozin, pyrachlophos, pyradaphenthion, pyresmethrin, pyrethrum, pyridaben, pyrimidifen, pyriproxifen, quinalphos,

RH 5992, salithion, sebufos, silafluofen, sulphotep, sulprofos, tebufenozid, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

The active compound combinations can be used as such, in the form of their formulations or as the use forms prepared therefrom, such as ready-to-use solutions, emulsifiable concentrates, emulsions, suspensions, wettable powders, soluble powders and granules. They are used in the customary manner, for example by watering, spraying, atomizing, scattering, spreading, and as a powder for dry seed treatment, a solution for seed treatment, a water-soluble powder for seed treatment, a water-soluble powder for slurry treatment, or by encrusting.

In the treatment of parts of plants, the active compound concentrations in the use forms can be varied within a relatively wide range. In general, they are between 1 and 0.0001% by weight, preferably between 0.5 and 0.001%.

In the treatment of the seeds, amounts of active compound of generally from 0.001 to 50 g per kilogram of seed, preferably from 0.01 to 10 g, are required.

In the treatment of the soil, active compound concentrations of from 0.00001 to 0.1% by weight, preferably 0.0001 to 0.02% by weight, are required at the site of action.

The good fungicidal activity of the active compound combinations according to the invention is evident from the examples below. While the individual active compounds exhibit weaknesses with regard to the fungicidal activity, the combinations have an activity which exceeds a simple addition of activities.

A synergistic effect of fungicides is always present when the fungicidal activity of the active compound combinations exceeds the total of the activities of the active compounds when applied individually.

The expected activity for a given combination of two active compounds can be calculated as follows (cf. Colby, S.

R., "Calculating Synergistic and Antagonistic Responses of Herbicide Combinations", Weeds 15, pages 20–22, 1967):

If
X is the efficacy, expressed in % of the untreated control, when applying the active compound A at a concentration of m ppm,
Y is the efficacy, expressed in % of the untreated control, when applying the active compound B at a concentration of m ppm,
E is the expected efficacy, expressed in % of the untreated control, when applying the active compounds A and B at a concentration of m and n ppm, $$E = X + Y - \frac{X \cdot N}{100}.$$

If the actual fungicidal activity exceeds the calculated value, then the activity of the combination is superadditive, i.e. a synergistic effect exists. In this case, the efficacy which was actually observed must be greater than the value for the expected efficacy (E) calculated from the abovementioned formula.

What is claimed is:

1. An active compound combination comprising a compound of the formula (I)

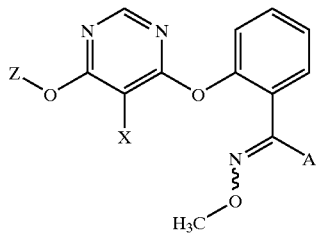

(I)

wherein
Z represents optionally substituted phenyl,
X represents halogen and
A represents —COOCH$_3$ or —CO—NH—CH$_3$; and
one mixing partner selected from the group consisting of tebuconazole, triadimefon, triadimenol, epoxiconazole, metconazole, fluquinconazole, cyproconazole, penconazole, flusilazole, propiconazole, bitertanol, difenoconazole, and 2-(1-chloro-cyclopropyl)-1-(2-chlorophenyl)-3-(5-mercapto-1,2,4-triazol-1-yl)-propan-2-ol,
wherein the weight ratio of the compound of the formula (I) to the mixing partner is 20:1 to 1:50.

2. A method for controlling fungi, comprising applying a fungicidally effective amount of the active compound combination of claim 1 to at least one of the fungi and its habitat.

3. A process for preparing fungicidal compositions, comprising mixing the active compound combination of claim 1 with at least one of extenders and surfactants.

4. A composition comprising the active compound combination of claim 1 and at least one member selected from the group consisting of extenders and surfactants.

5. The active compound combination of claim 1, wherein Z represents

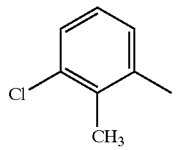

X represents fluorine
A represents CO—NH—CH$_3$; and the mixing partner is tebuconazole.

* * * * *